United States Patent [19]

Gedridge, Jr. et al.

[11] Patent Number: 5,164,524
[45] Date of Patent: Nov. 17, 1992

[54] PROCESS FOR PREPARING TETRA (ORGANYL) TELLURIDE COMPOUNDS

[75] Inventors: Robert W. Gedridge, Jr.; Kelvin T. Higa, both of Ridgecrest, Calif.

[73] Assignee: The United States of America as represented by the Secretary of the Navy, Washington, D.C.

[21] Appl. No.: 774,399

[22] Filed: Oct. 10, 1991

Related U.S. Application Data

[62] Division of Ser. No. 475,563, Feb. 6, 1990.

[51] Int. Cl.$^5$ .................. C07F 7/08; C07C 395/00
[52] U.S. Cl. .................................. 556/423; 562/899
[58] Field of Search .................... 562/899; 556/423

[56] References Cited

PUBLICATIONS

Hellwinkel et al., Chem. Ber., vol. 101, pp. 574–584 (1968).
Cohen et al., J. Organomet. Chem., vol. 11, pp. 563–566 (1968).

Primary Examiner—José G. Dees
Assistant Examiner—Porfirio Nazario
Attorney, Agent, or Firm—Stuart H. Nissim; Melvin J. Sliwka; John Forrest, Jr.

[57] ABSTRACT

Compounds and process for preparation and isolation of tetraorganyl tellurium compounds including: tetraalkyl tellurium and tetraalkenyl tellurium. The products remain relatively stable in the absence of light and air.

23 Claims, No Drawings

PROCESS FOR PREPARING TETRA (ORGANYL) TELLURIDE COMPOUNDS

This is a divisional of application: Ser. No. 07/475,563 filed on Feb. 6, 1990, now allowed.

BACKGROUND OF THE INVENTION

This invention relates to organotellurium compounds and is particularly directed to certain tetra(organyl) tellurium (IV) compounds, especially tetraalkyl tellurium (IV) compounds and tetraalkenyl tellurium (IV) compounds (hereinafter collectively referred to as tetraorganyl tellurium) such as tetramethyl tellurium (IV), tetra(trimethylsilylmethyl) tellurium (IV), and tetravinyl tellurium (IV) (hereinafter respectively referred to as tetramethyl tellurium, tetra(trimethylsilylmethyl) tellurium and tetravinyl tellurium) and to a process for the preparation of the above compounds.

In spite of the malodorous nature, light sensitivity and toxicity associated with organotellurium compounds, these compounds have a variety of useful applications in organic synthesis, polymers, biochemistry and semiconductor film growth, particularly as source compounds for the metal-organic chemical vapor deposition (MOCVD) of mercury cadmium telluride semiconductor films.

Diorganyl tellurium compounds have been obtained by reducing TeCl4 or diorqanyl tellurium dihalides with Grignard reagents or organolithium reagents. The amount of alkylating reagents used was sufficient to form tetraorganyl tellurium intermediates which instantaneously decomposed by reductive elimination to yield the diorganyl tellurium compounds. Tetraaryl tellurium (IV) compounds have previously been prepared; however, other tetraorganyl tellurium compounds, specifically tetraalkyl tellurium compounds and tetraalkenyl tellurium compounds such as tetramethyl tellurium [(CH3)4Te], tetra(trimethylsilylmethyl) tellurium [((CH3)3SiCH2)4Te], and tetravinyl tellurium, [(CH2=CH)4Te] were believed to be too unstable to isolate and had prior to the present invention never been isolated or characterized. Thus for example, while tetramethyl tellurium has been prepared in solution as an intermediate, it had never been isolated.

One object of the invention is the provision of a class of highly reactive organotellurium compounds.

Another object of the invention is to prepare and isolate certain tetraorganyl tellurium compounds.

A still further object of the invention is the preparation and isolation of tetramethyl tellurium, tetra(trimethylsilylmethyl) tellurium and tetravinyl tellurium.

Yet another object of the invention is the provision of procedure for the preparation of the above organotellurium compounds.

SUMMARY OF THE INVENTION

According to the invention, tetraorganyl tellurium compounds can be prepared and isolated by reacting tellurium tetrachloride TeCl4, with at least four molar proportions of organyl lithium or organyl magnesium halide in an inert atmosphere, and in the absence of light.

Preferably, the reaction is carried out using an excess of greater than four molar proportions of the organyl lithium or the organyl magnesium halide, and in a suitable solvent.

The tetraorganyl tellurium compounds are prepared and isolated in the absence of light and air, and remain relatively stable in the absence of light and air. These compounds readily decompose by reductive elimination, either in the presence of light or by heating, to form the corresponding diorganyl tellurium (II). The diorganyl tellurium compounds are more stable than the respective tetraorganyl tellurium compounds.

DETAILED DESCRIPTION OF THE INVENTION AND PREFERRED EMBODIMENTS

In preferred practice, tellurium tetrachloride is reacted with either an organyl lithium or organyl magnesium halide to produce the corresponding tetraorganyl tellurium; for example, tellurium tetrachloride is reacted with methyl lithium to produce tetramethyl tellurium, tellurium tetrachloride is reacted with trimethylsilylmethyl magnesium chloride to produce tetra(trimethylsilylmethvl-) tellurium, and tellurium tetrachloride is reacted with vinyl magnesium bromide to produce tetravinyl tellurium, according to the reaction schemes noted below:

$$TeCl_4 + 4(R)Li \rightarrow (R)_4Te + 4LiCl \qquad (1)$$

wherein
R is an Organyl group
For example:

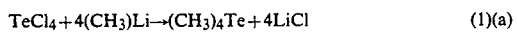
$$TeCl_4 + 4(CH_3)Li \rightarrow (CH_3)_4Te + 4LiCl \qquad (1)(a)$$

$$TeCl_4 + 4(R)MgX \rightarrow (R)_4Te + 4MgXCl \qquad (2)$$

wherein
R is an Organyl group
X is a Halide
For example:

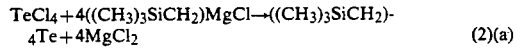
$$TeCl_4 + 4((CH_3)_3SiCH_2)MgCl \rightarrow ((CH_3)_3SiCH_2)_4Te + 4MgCl_2 \qquad (2)(a)$$

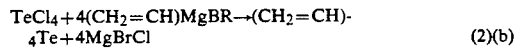
$$TeCl_4 + 4(CH_2=CH)MgBR \rightarrow (CH_2=CH)_4Te + 4MgBrCl \qquad (2)(b)$$

In the above reactions, a 1:4 molar ratio of tellurium tetrachloride to organyl lithium, methyl lithium, organyl magnesium halide, trimethylsilylmethyl magnesium chloride, or vinyl magnesium bromide is employed. However, it is preferred to employ a small excess of the organyl lithium, methyl lithium, organyl magnesium halide, trimethylsilylmethyl magnesium chloride, or vinyl magnesium bromide, e.g., 4.2 moles of methyl lithium, trimethylsilylmethyl magnesium chloride, or vinyl magnesium bromide, per mole of TeCl4, in the event that the organyl lithium, methyl lithium, organyl magnesium halide, trimethylsilylmethyl- magnesium chloride, or vinyl magnesium bromide compounds are not sufficiently pure.

In the above equation (1)(a), methyl magnesium halide, a Grignard reagent, e.g., methyl magnesium chloride, methyl magnesium bromide or methyl magnesium iodide, can be employed in place of methyl lithium. However, methyl lithium is preferred for the production of tetramethyl tellurium.

In equation (2)(a) above, for the production of tetra(-trimethylsilylmethyl) tellurium, trimethylsilylmethyl magnesium chloride or an equivalent Grignard reagent, e.g., trimethylsilylmethyl magnesium bromide or trimethylsilylmethyl magnesium iodide, is the preferred reactant for the reaction with TeCl$_4$. However, trimethylsilylmethyl lithium or any other equivalent trimethylsilylmethyl compound can be employed.

In equation (2)(b) above, for the production of tetravinyl tellurium, vinyl magnesium bromide or an equivalent Grignard reagent, e.g., vinyl magnesium chloride or vinyl magnesium iodide is the preferred reactant for the reaction with TeCl$_4$. However, vinyl lithium or any other equivalent vinyl compound can be employed.

The reactions, as illustrated in equations (1), (1)(a), (2), (2)(a), or (2)(b) above, for the production of tetraorganyl tellurium, tetramethyl tellurium, tetraorganyl tellurium, tetra(trimethylsilylmethyl) tellurium, or tetravinyl tellurium, are commenced at low temperature ranging from about −100° C. to about 25° C. If the above reactions are carried out at higher temperature, the corresponding diorganyl tellurium, dimethyl tellurium, bis(trimethylsilyl-methyl) tellurium, or divinyl tellurium derivatives will also be produced, or other side reactions will occur. After the reactions have proceeded to form the tetraorganyl tellurium, tetramethyl tellurium, tetra(trimethylsilylmethyl) tellurium, or tetravinyl tellurium product, the reaction mixture is warmed to room temperature and is stirred; and if a Grignard reagent was used, 1,4-dioxane is added to remove magnesium salts. The slurry is then cooled down again within the above noted −100° C. to 25° C. range, so that all of the salts will precipitate out of solution. The reaction mixture is then filtered to remove precipitated salts. The resulting solution containing the tetraorganyl tellurium, tetramethyl tellurium, tetra(trimethylsilylmethyl) tellurium, or tetravinyl tellurium is then vacuum distilled to remove the solvent, and the crude product purified, e.g., by vacuum distillation for the liquid product, tetramethyl tellurium, or by fractional recrystallization for the solid product, tetra(trimethylsilylmethyl) tellurium.

The above reactions (1), (1)(a), (2), (2)(a), and (2)(b) are exothermic and the resulting products are very reactive and, therefore, are preferably carried out at low temperature within the range noted above; which also enhances yield. Both the tetramethyl tellurium and the tetra(trimethylsilylmethyl) tellurium are more stable than the tetravinyl tellurium, and the reaction for preparing tetramethyl tellurium and tetra(trimethylsilylmethyl) tellurium may be carried out at reaction temperatures sufficiently low to prevent solvent refluxing of the reaction (as high as approximately 25° C.). However, for preparation of tetravinyl tellurium, the temperature should be maintained below about 0° C.

In the above reactions illustrated by (1), (1)(a), (2), (2)(a), and (2)(b), polar solvents such as diethyl ether and THF (tetrahydrofuran) can be employed. A mixture of diethyl ether and THF can also be employed as a solvent. However, it is convenient to employ diethyl ether as a solvent in the reaction for producing tetramethyl tellurium and tetra(trimethyl-silyl-methyl) tellurium since methyl lithium and trimethylsilylmethyl magnesium chloride are generally available in diethyl ether solution, and it is convenient to employ THF in the reaction for producing tetravinyl tellurium, since vinyl magnesium bromide is available commercially in THF. Other suitable polar solvents also can be employed.

The tetraorganyl tellurium compounds, tetramethyl tellurium, tetra(trimethylsilylmethyl) tellurium, and tetravinyl tellurium products are extremely light sensitive and require their preparation and isolation in the absence of light. Pressure is not a critical factor in carrying out the reactions illustrated in (1), (1)(a), (2), (2)(a), and (2)(b) above, and generally ambient pressure is employed, although higher or lower pressures can be utilized.

The yields obtained for production of tetramethyl tellurium and tetra(trimethylsilylmethyl) tellurium by the reactions illustrated in (1)(a) and (2)(a) above are quite high and generally are in the range of about 60 to about 80 percent, based on TeCl$_4$. However, for production of tetravinyl tellurium by the reaction illustrated in (2)(b) above, the yields of product obtained are usually not greater than about 38% based on TeCl$_4$, since reactions in a Grignard reagent such as vinyl magnesium bromide result in significantly lower yields and tetravinyl tellurium is less stable.

The invention compound $(CH_3)_4Te$ is a volatile organotellurium compound. It is a malodorous liquid, which is extremely pyrophoric and can explode when in contact with air or oxygen. This organotellurium compound may be used as an explosive or in pyrotechnic applications, and may also be employed in catalysis, polymerization reactions, coordination chemistry or as a source compound for pyrolytic and photolytic MOCVD of mercury cadmium telluride semiconductor films, and as an oxidizing agent in organic syntheses. It is an excellent free-radical initiator in polymerization catalysis. Several different organic polymers have been made with tetramethyl tellurium.

The $((CH_3)_3SiCH_2)_4Te$ product is less volatile than both $(CH_3)_4Te$ and $(CH_2=CH)_4Te$. It is a malodorous solid that is stable at 0° C. or lower in the absence of light. It has potential application in catalysis, polymerization reactions, coordination chemistry and as an oxidizing agent in organic syntheses It is a free-radical initiator in polymerization catalysis. Several different organic polymers have been made with it.

The $(CH_2=CH)_4Te$ product is also in the form of a malodorous liquid, but is not as volatile or as reactive as $(CH_3)_4Te$. It is not pyrophoric. However, it also has potential application as an oxidizing agent in organic syntheses, in catalysis, polymerization reactions, and coordination chemistry.

The tetraorganyl tellurium, tetramethyl tellurium, tetra(trimethylsilylmethyl) tellurium, and tetravinyl tellurium products of the invention can be converted to the corresponding diorganyl tellurium, dimethyl tellurium, bis(trimethylsilylmethyl) tellurium, and divinyl tellurium compounds. Such reactions can be carried out by exposure to light or by heating the tetraorganyl tellurium, tetramethyl tellurium, tetra(trimethylsilylmethyl) tellurium, or tetravinyl tellurium products respectively, according to the reaction schemes:

(3)

wherein R is an Organyl group.

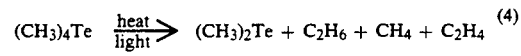

(4)

(5)

-continued

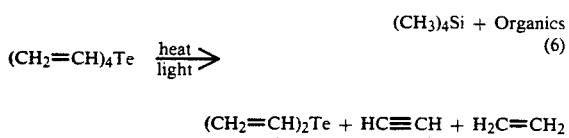

$$(CH_2=CH)_2Te + HC\equiv CH + H_2C=CH_2$$

The decomposition reaction (4) shown above for production of dimethyl tellurium is carried out at a temperature of about 105° C. or higher; the decomposition reaction (5) above for the production of bis(trimethylsilylmethyl) tellurium is carried out by heating at a temperature of 55° C. or higher: and, the decomposition reaction (6) above for production of divinyl tellurium is carried out by heating at a temperature of about 40° C. or higher.

The decomposition reactions (3), (4), (5), and (6) above, by exposure to light, may be carried out at room temperature, above room temperature, or below room temperature.

EXAMPLES

Examples of practice of the invention for production of tetramethyl tellurium, tetra(trimethylsilylmethyl) tellurium, and tetravinyl tellurium are set forth below, it being understood that these examples are only illustrative and are not intended as limitative of the invention.

All procedures in the examples were performed under an inert atmosphere, such as prepurified argon gas.

All reaction vessels used in the examples below were covered with aluminum foil to prevent the infiltration of light. (However, the aluminum foil was removed periodically to observe changes in reaction conditions in the vessel).

All procedures in the examples below were performed in the absence of light. Sunlight is excluded as it is extremely fatal to the reaction products. Ambient room light, while not as deleterious as sunlight and need not be totally excluded, is preferably kept only at a level sufficient to observe changes in reaction conditions.

EXAMPLE 1

Tetramethyl Tellurium

To a stirring suspension of pulverized $TeCl_4$(10.0 g, 37 mmol) in 40 ml of diethyl ether at $-78°$ C. was added dropwise 4.2 equivalents of $(CH_3)Li$ in diethyl ether (1.4M, 111 ml, 155 mmol). The suspension turned brown initially, then light yellow after the addition was complete. The reaction was warmed to room temperature and stirred 12 hrs. The resulting suspension was cooled to $-78°$ C. and filtered to yield a yellow supernatant. The white precipitate was washed with 25 ml of diethyl ether. The combined diethyl ether solutions were fractionally distilled at 32° C. under slight vacuum to remove the solvent. The crude product was collected at $-198°$ C. under vacuum, then purified by vacuum distillation (45°-46° C., 20 torr). Pure $(CH_3)_4Te$ was obtained as an extremely air-, light-, and heat-sensitive, malodorous pyrophoric yellow-orange liquid (5.39 g, 28.7 mmol, 77% yield based on $TeCl_4$). Anal. Calcd. for $C_4H_{12}Te$: Te;67.97% Found: Te;68.36%. A sample for C/H analysis exploded upon exposure to oxygen. $^{13}C$ NMR, $^1H$ NMR and $^{125}Te$ NMR were characteristic of $(CH_3)_4Te$.

EXAMPLE 2

Tetra(trimethylsilylmethyl) Tellurium

To a stirring suspension of pulverized $TeCl_4$(3.5g, 13 mmol) in 25 mL of diethyl ether was added dropwise with stirring 4.2 equivalents of $(CH_3)_3SiCH_2MgCl$ in diethyl ether(1.0M, 55 ml, 55 mmol) at $-78°$ C. The suspension turned brown initially, then light-yellow after the addition was complete. After stirring the yellow slurry for 2 hours at 0.C, 3mL of 1,4-dioxane was added to precipitate the magnesium salts. The mixture was stirred for 1 hour at 0° C., cooled to $-78°$ C. and then filtered cold to yield a yellow supernatant. The white precipitate was washed with two 25mL portions of pentane. The solvent of the combined solutions was removed under vacuum at 0° C. to yield a yellow solid. The extremely air-, light-, and heat-sensitive product was then further dried under vacuum for 30 minutes at room temperature to yield $((CH_3)_3SiCH_2)_4Te$ (4.7 g., 9.8 mmol, 75% yield based on $TeCl_4$). The product was purified by fractional recrystallization from pentane. $^{13}C$ NMR, $^1H$ NMR and $^{125}Te$ NMR were characteristic of $((CH_3)_3SiCH_2)_4Te$.

EXAMPLE 3

Tetravinyl Tellurium

To a stirring suspension of pulverized $TeCl_4$(7.0 g, 26 mmol) in 30 ml of THF, was added dropwise with stirring 4.2 equivalents of $(CH_2=CH)MgBr$ in THF (1.0M, 109 ml, 109 mmol) at $-78°$ C. in the dark. The suspension turned brown initially, then yellow after the addition was complete. After stirring the yellow slurry for 2.5 hours at room temperature, 10 ml of 1,4-dioxane was added to precipitate the magnesium salts. The mixture was stirred for 45 minutes at room temperature, cooled to $-78°$ C. and then filtered cold to yield a yellow supernatant. The white precipitate was washed with two 25 ml portions of hexane. The solvent of the combined solutions was fractionally distilled under vacuum at room temperature to yield an oily yellow residue. The product was then extracted with four 25 ml portions of pentane and filtered. The solvent was removed under vacuum and the crude product was collected in a $-198°$ C. trap. The product was stirred under vacuum (10 torr) at room temperature for 1 hour to remove traces of solvent. A pale yellow fraction of $(CH_2=CH)_2Te$(0.11 g,0.6 mmol, 2% yield based on $TeCl_4$) was collected at 3.5 torr at 27°-29° C. $(CH_2=CH)_4Te$ was isolated as a yellow malodorous liquid (2.3 g, 9.9 mmol, 38% yield based on $TeCl_4$). $(CH_2=CH)_4Te$ is an extremely air-, light-, and heat-sensitive liquid that gradually decomposes to $(CH_2=CH)_2Te$, ethylene and acetylene at room temperature in the presence or absence of light. $^{13}C$ NMR, $^1H$ NMR and $^{125}$ Te NMR were characteristic of $(CH_2=CH)_4Te$.

From the foregoing, it is seen that the present invention provides for the preparation and isolation of highly reactive compounds such as tetramethyl tellurium, tetra(trimethylsilylmethyl) tellurium, and tetravinyl tellurium, having a variety of uses, as noted above, including use as source compounds for mercury cadmium telluride infrared detectors, as well as having utility as polymerization catalysts, co-polymerization reagents, or alkylating agents useful for chemical synthesis.

Since various changes and modifications can be made in the invention without departing from the spirit of the invention, the invention is not to be taken as limited except by the scope of the appended claims.

What is claimed is:

1. A process for preparing compounds having the formula $(R)_4Te$ which comprises reacting $TeCl_4$ with at least four molar proportions of a compound selected from the group consisting of RLi and RMgX, in the absence of light and air, and isolating said compounds, wherein R is a non-aryl organyl group X is a halide.

2. The process of claim 1 for preparing compounds having the formula $(R)_4Te$ wherein, R is selected from the group consisting of alkyl and alkenyl.

3. The process of claim 1 for preparing compounds having the formula $(R)_4Te$ wherein, R is selected from the group consisting of methyl, trimethylsilylmethyl, and vinyl.

4. The process of claim 1 for preparing compounds having the formula $(R)_4Te$ which comprises reacting the $TeCl_4$ with an excess of greater than four molar proportions of said organyl lithium compound in a suitable solvent.

5. The process of claim 1 for preparing compounds having the formula $(R)_4Te$ which comprises reacting the $TeCl_4$ with an excess of greater than four molar proportions of said organyl magnesium halide compound in a suitable solvent.

6. The process of claim 4 for preparing tetramethyl tellurium which comprises reacting the $TeCl_4$ with greater than four molar proportions of methyl lithium in the absence of light and air, and isolating said compound.

7. The process of claim 5 for preparing tetra(trimethylsilylmethyl) tellurium which comprises reacting the $TeCl_4$ with greater than four molar proportions of trimethylsilylmethyl magnesium chloride in the absence of light and air, and isolating said compound.

8. The process of claim 5 for preparing tetravinyl tellurium which comprises reacting the $TeCl_4$ with greater than four molar proportions of vinyl magnesium bromide in the absence of light and air, and isolating said compound.

9. The process of claim 1 for preparing compounds having the formula $(R)_4Te$, wherein the process is performed in a suitable solvent, wherein said solvent is selected from the group consisting of diethyl ether, THF, and mixtures thereof.

10. A process for preparing tetramethyl tellurium which comprises reacting $TeCl_4$ with methyl lithium in a molar proportion of 1 to about 4.2 at temperatures between about $-100°$ C. and about $25°$ C., in a suitable solvent and in the absence of light and air, forming tetramethyl tellurium, and recovering said tetramethyl tellurium.

11. The process of claim 10 for preparing tetramethyl tellurium, said solvent being selected from the group consisting of diethyl ether, THF, and mixtures thereof.

12. A process for preparing tetra(trimethylsilylmethyl) tellurium which comprises reacting $TeCl_4$ with trimethylsilylmethyl magnesium chloride in a molar proportion of 1 to about 4.2 at temperatures between about $-100°$ C. and about $25°$ C. in a suitable solvent and in the absence of light and air, forming tetra(trimethylsilylmethyl) tellurium, and recovering said tetra(trimethylsilylmethyl) tellurium.

13. The process of claim 12 for preparing tetra(trimethylsilylmethyl) tellurium, said solvent being selected from the group consisting of: diethyl ether, THF, and mixtures thereof.

14. A process for preparing tetravinyl tellurium which comprises reacting $TeCl_4$ with vinyl magnesium bromide in a molar proportion of 1 to about 4.2 at reduced temperatures between about $-100°$ C. and about $0°$ C., in a suitable solvent and in the absence of light and air, forming tetravinyl tellurium, and recovering said tetravinyl tellurium.

15. The process of claim 14 for preparing tetravinyl tellurium, said solvent being selected from the group consisting of diethyl ether, THF, and mixtures thereof.

16. The process of claim 9 wherein the process is performed at temperatures below room temperature.

17. The process of claim 16, for preparing compounds having the formula $(R)_4Te$ wherein, R is selected from the group consisting of alkyl and alkenyl.

18. The process of claim 16 for preparing compounds having the formula $(R)_4Te$ wherein, R is selected from the group consisting of methyl, trimethylsilylmethyl, and vinyl.

19. The process of claim 16 for preparing compounds having the formula $(R)_4Te$ which comprises reacting the $TeCl_4$ with an excess of greater than four molar proportions of said organyl lithium compound in a suitable solvent.

20. The process of claim 16 for preparing compounds having the formula $(R)_4Te$ which comprises reacting the $TeCl_4$ with an excess of greater than four molar proportions of said organyl magnesium halide compound in a suitable solvent.

21. The process of claim 16 for preparing tetramethyl tellurium which comprises reacting the $TeCl_4$ with greater than four molar proportions of methyl lithium in the absence of light and air at temperatures sufficiently low to prevent solvent refluxing, and isolating said compound.

22. The process of claim 16 for preparing tetra(trimethyl-silylmethyl)-tellurium which comprises reacting the $TeCl_4$ with greater than four molar proportions of trimethylsilylmethyl magnesium chloride in the absence of light and air at temperatures sufficiently low to prevent solvent refluxing, and isolating said compound.

23. The process of claim 16 for preparing tetravinyl tellurium which comprises reacting the $TeCl_4$ with greater than four molar proportions of vinyl magnesium bromide in the absence of light and air at temperatures sufficiently low to prevent solvent refluxing, and isolating said compound

* * * * *